(12) United States Patent
Leonard (10) Patent No.: US 9,987,458 B2
(45) Date of Patent: Jun. 5, 2018

(54) LAMP WITH VARIABLE FLICKERING FREQUENCY

(76) Inventor: John-Mark Leonard, Niagara Falls (CA)

( * ) Notice: Subject to any disclaimer, the term of this patent is extended or adjusted under 35 U.S.C. 154(b) by 476 days.

(21) Appl. No.: 13/341,790

(22) Filed: Dec. 30, 2011

(65) Prior Publication Data

US 2013/0172663 A1 Jul. 4, 2013

(51) Int. Cl.
| | | |
|---|---|---|
| *A61M 21/02* | (2006.01) | |
| *F21S 6/00* | (2006.01) | |
| *F21V 14/08* | (2006.01) | |
| *F21S 10/06* | (2006.01) | |
| *A61M 21/00* | (2006.01) | |

(52) U.S. Cl.
CPC ............. *A61M 21/02* (2013.01); *F21S 6/002* (2013.01); *F21S 10/063* (2013.01); *F21V 14/08* (2013.01); *A61M 2021/0044* (2013.01)

(58) Field of Classification Search
CPC .............. A61M 21/00; A61M 2021/00; A61M 2021/0044
USPC ............... 600/26, 27; 362/35, 227; 313/149; 314/69–76
See application file for complete search history.

(56) References Cited

U.S. PATENT DOCUMENTS

| | | | | |
|---|---|---|---|---|
| 5,304,112 A | * | 4/1994 | Mrklas et al. | 600/27 |
| 5,552,975 A | * | 9/1996 | Ho | 362/324 |
| 2006/0109653 A1 | * | 5/2006 | Takacs | 362/293 |
| 2008/0165527 A1 | * | 7/2008 | VanderSchuit | 362/133 |
| 2010/0161010 A1 | * | 6/2010 | Thomas | 607/88 |
| 2011/0301406 A1 | * | 12/2011 | Ehara | 600/27 |

OTHER PUBLICATIONS

Brion Gysin, Dreamachine Plans, www.ubu.com/papers/Gysin-Brion_DreamMachine-Plans.pdf; Apr. 25, 2012.
Coolcat's Dream Machine Plan; www.angelfire.com/mt/GardenofDelights/dreamachine.html; Apr. 26, 2012.
LVB Research; The Dreamachine and Brainwave Entertainment; www.lvb-research.blogspot.ca/2010/05/dreamachine-and-brainwave-entertainment.html; Apr. 26, 2012.
Mindalive Inc.; David PAL36 with CES; www.mindalive.com/Products_DAVID_PAL36.htm; Apr. 27, 2012.

(Continued)

*Primary Examiner* — Christine H Matthews
(74) *Attorney, Agent, or Firm* — Steven M. Greenberg; CRGO Law (57) ABSTRACT

A lamp for generating flickering at a selectable frequency corresponding to a desired human brainwave state comprises a base supporting a light source, a shade having a plurality of regularly circumferentially spaced apertures defined therein and a drive mechanism for rotating the shade about the light source. At least one speed control is coupled to the drive mechanism for controlling the rotational speed of the shade. Rotation of the shade while the light source is emitting light produces flickering for an observer looking at the lamp from a fixed position, and the speed control can be used to select a rotational speed of the shade to produce flickering at a frequency corresponding to a pre-selected human brainwave state.

20 Claims, 4 Drawing Sheets

(56) References Cited

OTHER PUBLICATIONS

CYBORG/ASM; Brain-Wave Machine; www.hackcanada.com/homegrown/wetware/brainwave/index.html; Apr. 27, 2012.
Kevin S. Meredith; Build Your Own Pocket-Sized Dreamachine!; www.interpc.fr/mapage/westernlands/dreamachinekevin.html; Apr. 26, 2012.
Simon Owen; Electronic Dreamachine; www.inter-zone.org/dreamachine3.html; Apr. 27, 2012.
Dreamachine or Other Stroboscopic Device Under Influence; www.dmt-nexus.me/forum/default.aspx?g=posts&t=7838; May 9, 2012.
Untitled; www.dreamachine.ca/dreamachine_browser.html; Apr. 27, 2012.

* cited by examiner

LAMP WITH VARIABLE FLICKERING FREQUENCY

TECHNICAL FIELD

This disclosure relates to lamps, and more particularly to flickering lamps.

BACKGROUND

Human beings are believed to have a number of brainwave states that correspond to specific frequency ranges. The "delta" brainwave state, corresponding to a frequency range of up to about 3 or 4 Hz, is associated with deep sleep and deep relaxation. The "theta" brainwave state, corresponding to a frequency range from about 3 or 4 Hz to about 7 or 8 Hz, is associated with drowsiness, dreaming sleep, daydreaming and creativity, and the "alpha" brainwave state, corresponding to a frequency range from about 7 or 8 Hz to about 12 or 13 Hz, is associated with awake relaxation and meditation. The "beta" brainwave state, corresponding to a frequency range from about 12 or 13 Hz to about 30 Hz, is considered a normal, fully alert state, typically associated with thinking and concentration. The "gamma" brainwave state begins above about 30 Hz.

It is believed that human brainwave frequencies can synchronize with external stimuli at particular frequencies. This process is referred to as brainwave entrainment. Thus, it is believed that exposure to audio or visual stimuli at a frequency corresponding to a given human brainwave state can facilitate a human brain entering the brainwave state associated with that frequency.

One notable example of a device designed for facilitating entry into a desired human brainwave state is the flickering lamp developed by artist Brion Gysin and mathematician Ian Sommerville and known as the "dreamachine". The "dreamachine" was constructed by forming a hollow cylinder having equally spaced apertures defined therein, supporting the cylinder on a turntable such as a record player, and suspending a light bulb inside the cylinder. Because of the rotation of the cylinder, light emitted from the apertures would produce a flickering effect for a stationary observer, and the rotation speed and aperture spacing of the "dreamachine" were selected to generate a flicker frequency between about 7 or 8 Hz and about 12 or 13 Hz, corresponding to the alpha brainwave state. It is believed that a user can be guided into an alpha brainwave state by sitting close to the "dreamachine" and "viewing" the rotating cylinder with the user's eyes closed.

Other techniques for attempting brainwave entrainment use electronically controlled flickering light sources, sometimes in conjunction with audio stimuli (i.e. "binaural beats") at the same frequency range, in an effort to selectably facilitate entry into a desired human brainwave state. For example, recordings may produce the visual stimuli at particular frequencies when played back on a television or computer monitor, or electronically controlled light sources such as light-emitting diodes (LEDs) producing pulses at specific frequencies can be integrated into goggles.

SUMMARY

A lamp for generating flickering at a selectable frequency corresponding to a desired human brainwave state comprises a base, a light source, a shade, a drive mechanism and a speed control for the drive mechanism. The light source is supported by the base. The shade has a plurality of regularly circumferentially spaced apertures defined therein, circumferentially surrounds the light source and is rotatably supported by the base for rotation about the light source. The drive mechanism is supported by the base and is drivingly coupled to the shade for rotating the shade about the light source. The drive mechanism and the light source are coupled to at least one power connector for supplying power to the drive mechanism and the light source. Rotation of the shade while the light source is emitting light produces flickering for an observer looking at the lamp from a fixed position. The lamp includes at least one speed control coupled to the drive mechanism for controlling the drive mechanism to select a rotational speed of the shade to selectively produce one of at least flickering within a first predetermined frequency range corresponding to a first pre-selected human brainwave state and flickering within a second predetermined frequency range corresponding to a second pre-selected human brainwave state. The first and second pre-selected human brainwave states are different from one another.

In some embodiments, the at least one speed control controls the drive mechanism to select the rotational speed of the shade to also selectively produce flickering within a third predetermined frequency range corresponding to a third pre-selected human brainwave state, or to selectively produce flickering within a third predetermined frequency range corresponding to a third pre-selected human brainwave state and flickering within a fourth predetermined frequency range corresponding to a fourth pre-selected human brainwave state.

The frequency ranges may be selected from the group consisting of below 4 Hz wherein the corresponding pre-selected human brainwave state is a delta brainwave state, between about 4 to about 7 Hz wherein the corresponding pre-selected human brainwave state is a theta brainwave state, between about 7 to about 13 Hz wherein the corresponding pre-selected human brainwave state is an alpha brainwave state, and between about 13 to about 30 Hz wherein the corresponding pre-selected human brainwave state is a beta brainwave state.

In one particular embodiment, the first predetermined frequency range is between about 4 to about 7 Hz and the corresponding first pre-selected human brainwave state is a theta brainwave state, and the second predetermined frequency range is between about 7 to about 13 Hz and the corresponding second pre-selected human brainwave state is an alpha brainwave state.

In one embodiment, the drive mechanism comprises a variable speed motor and the at least one speed control is coupled to the drive mechanism by being coupled to the motor to control the speed of the motor. The at least one speed control may control the drive mechanism to select the rotational speed of the shade from among a plurality of discrete rotational speeds, or may control the drive mechanism to select the rotational speed of the shade from within at least one continuous range of rotational speeds.

The light source may comprise a single light element, or may comprise a plurality of individual light elements. The light source may be a variable intensity light source, and the lamp may further comprise a light control coupled to the light source for controlling the intensity of light emitted from the light source. The light source may also be a variable color light source, and the lamp may further comprise a light control coupled to the light source for controlling the color of light emitted from the light source. The light source may comprise at least one incandescent light source or at least one light-emitting diode.

A lamp for generating flickering at a selectable frequency corresponding to a desired human brainwave state comprises a base, a light source, a shade, a drive mechanism and a speed control for the drive mechanism. The light source is supported by the base. The shade has a plurality of regularly circumferentially spaced apertures defined therein, circumferentially surrounds the light source and is rotatably supported by the base for rotation about the light source. The drive mechanism is supported by the base and is drivingly coupled to the shade for rotating the shade about the light source. The drive mechanism and the light source are coupled to at least one power connector for supplying power to the drive mechanism and the light source. Rotation of the shade while the light source is emitting light produces flickering for an observer looking at the lamp from a fixed position. The lamp includes at least one speed control coupled to the drive mechanism for controlling the drive mechanism to select a rotational speed of the shade to selectively produce flickering within one of a plurality of different predetermined frequency ranges, with each predetermined frequency range corresponding to a different preselected human brainwave state.

The frequency ranges may be selected from the group consisting of below 4 Hz wherein the corresponding preselected human brainwave state is a delta brainwave state, between about 4 to about 7 Hz wherein the corresponding pre-selected human brainwave state is a theta brainwave state, between about 7 to about 13 Hz wherein the corresponding pre-selected human brainwave state is an alpha brainwave state, and between about 13 to about 30 Hz wherein the corresponding pre-selected human brainwave state is a beta brainwave state.

The at least one speed control may control the drive mechanism to select the rotational speed of the shade from among a plurality of discrete rotational speeds, or may control the drive mechanism to select the rotational speed of the shade from within at least one continuous range of rotational speeds.

The above summary is provided as an overview only, and is not intended to limit the scope of the appended claims in any way.

BRIEF DESCRIPTION OF THE DRAWINGS

These and other features of the invention will become more apparent from the following description in which reference is made to the appended drawings wherein.

DETAILED DESCRIPTION

Figure 1:
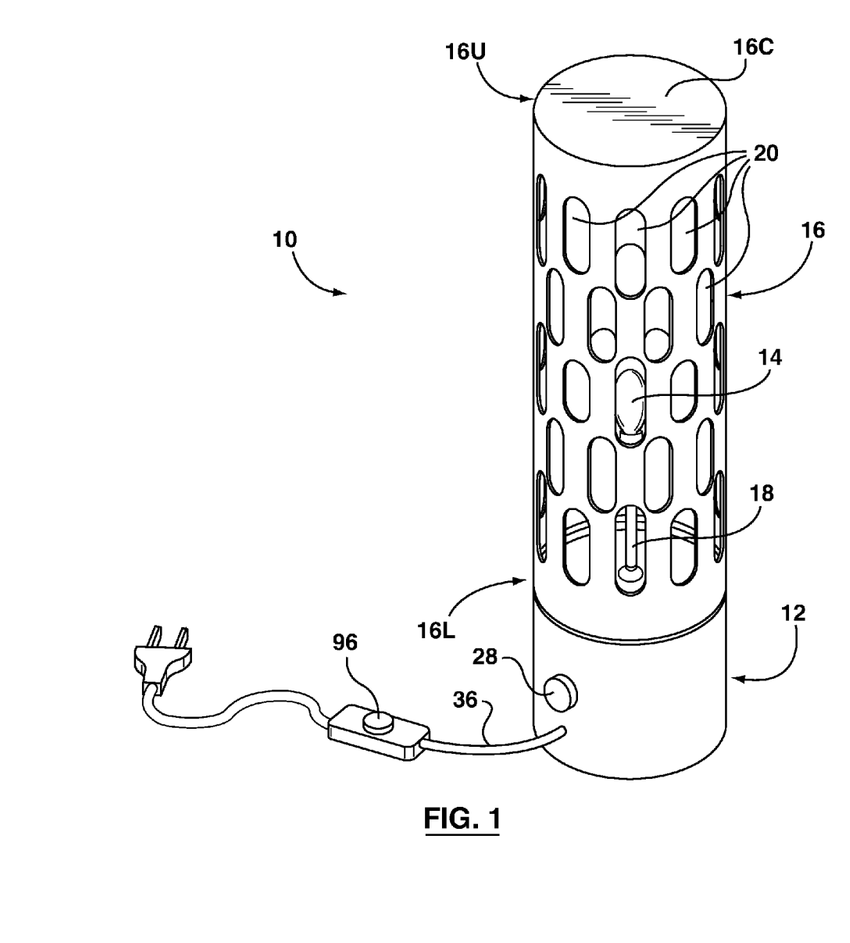
FIG. 1 is a perspective view of an exemplary lamp having a variable flickering frequency.
Figure 2A:
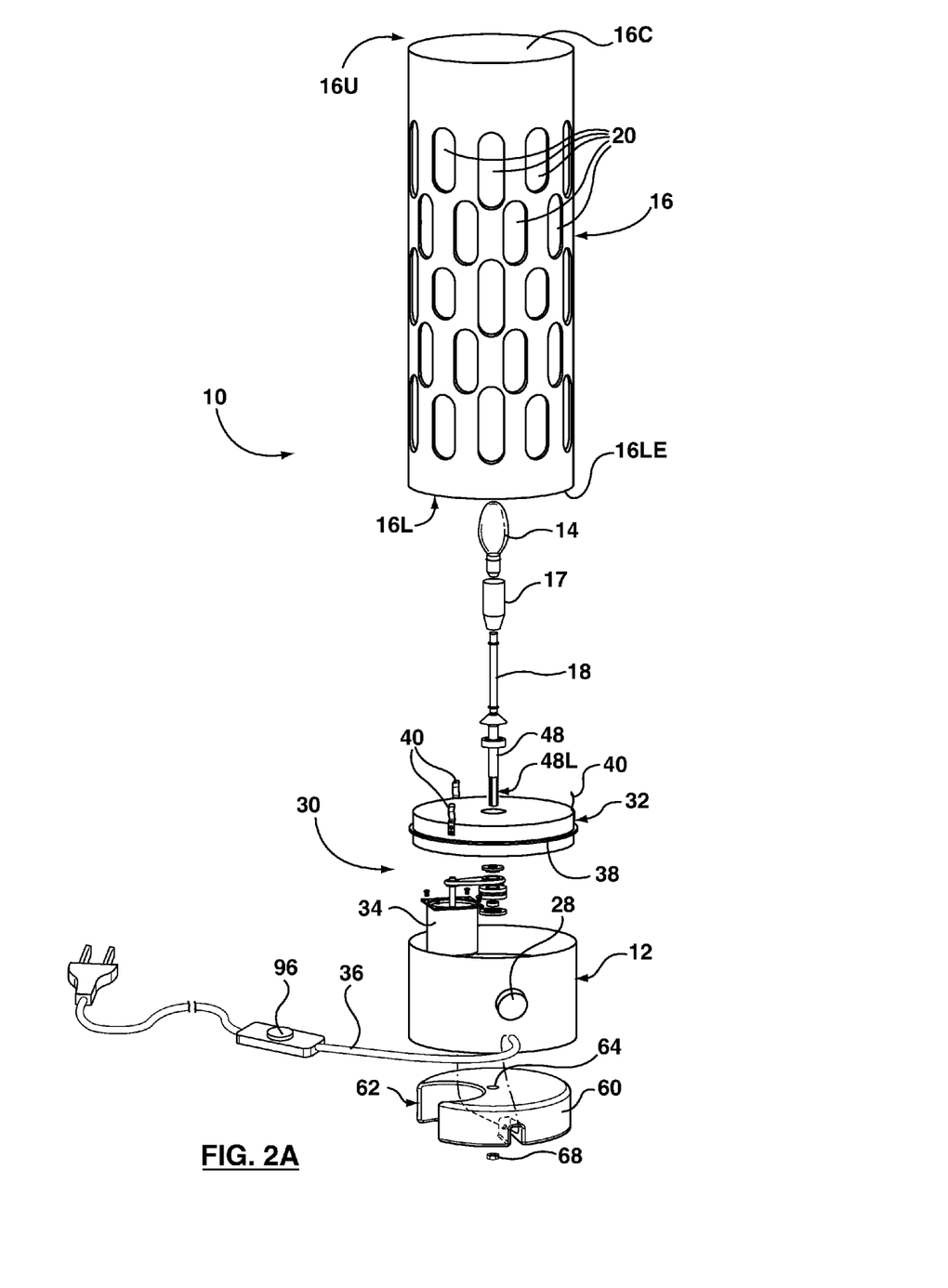
FIG. 2A is an exploded perspective view of the lamp of FIG. 1.

Reference is first made to FIG. 1. An exemplary embodiment of a lamp for generating flickering at a selectable frequency corresponding to a desired human brainwave state is indicated generally by the reference numeral 10. The lamp 10 comprises a generally cylindrical base 12, a light source 14 and a generally cylindrical shade 16. The light source 14 is received in a fitting 17 carried by a hollow spacer shaft 18 extending upwardly from the base 12. The shade 16 has a plurality of regularly circumferentially spaced apertures 20 defined therein and circumferentially surrounds the light source 14. The shade 16 has a closed upper end 16U having a canopy 16C extending thereacross and an open bottom end 16L that receives the spacer shaft 18, fitting 17 and the light source 14. The open bottom end 16L of the shade 16 defines a lower edge 16LE (FIG. 2) of the shade. The base 12 rotatably supports the shade 16 so that the shade 16 can rotate about the light source 14, relative to the base 12, and a speed control 28 is mounted on the base 12 for controlling the speed of rotation of the shade 16, as described in greater detail below.

Referring now to FIG. 2A, a drive mechanism 30 is disposed inside and supported by the base 12, and is drivingly coupled to the shade 16 for rotating the shade 16 about the light source 14. The speed control 28 is coupled to the drive mechanism 30 to control the speed of rotation of the shade 16; in the particular exemplary embodiment shown in the Figures, the speed control 28 is an electronic control coupled to a motor 34 forming part of the drive mechanism 30, and the speed control 28 controls the speed of rotation of the shade 16 by controlling the speed of the motor 34. The speed control 28 enables selection of one of a plurality of motor speeds and thereby enables selection of one of a plurality of rotational speeds for the shade 16. A power cord 36 extends into the base 12 to supply power to the drive mechanism 30 and the light source 14.

Rotating the shade 16 at a given speed while the light source 14 is emitting light will result in the apertures 20 in the shade 16 producing flickering for an observer looking at the lamp 10 from a fixed position. The frequency of the observed flickering will be a function of the rotational speed of the shade 16 relative to the base 12 together with the circumferential width and circumferential spacing of the apertures 20 in the shade 16. For a given arrangement of circumferential width and circumferential spacing of the apertures 20 in the shade 16, suitable rotational speeds can be determined for generating flickering at selected frequency ranges corresponding to desired human brainwave states. The speed control 28 is coupled to the drive mechanism to select a rotational speed of the shade 16 to selectively produce flickering within one of a plurality of different predetermined frequency ranges, with each predetermined frequency range corresponding to a different pre-selected human brainwave state. The speed control 28 can enable selection of rotation speeds producing flickering frequencies within two different frequency ranges, three different frequency ranges, or more than three frequency ranges. In one embodiment, the speed control 28 controls the drive mechanism to select the rotational speed of the shade 16 from among a plurality of discrete predefined rotational speeds, with each discrete rotation speed producing a corresponding predefined flickering frequency. For example, the speed control 28 may select from two or more discrete rotational speeds for the shade 16, with at least two of the discrete rotational speeds producing a flickering frequency corresponding to different pre-selected human brainwave states. In other embodiments, the speed control 28 controls the drive mechanism 30 to select the rotational speed of the shade 16 from within at least one continuous range of rotational speeds. In such embodiments, the speed control 28 can select from within ranges of rotational speeds producing frequency ranges that correspond to at least two different human brainwave states. The speed control 28 will typically include suitable markings or other indicia to indicate the current setting of the speed control, preferably by indicating at least the human brainwave state that corresponds to the flickering frequency produced at the rotational speed for that setting. In the illustrated embodiment the speed control 28 can also activate and deactivate the drive mechanism 30; in other embodiments the speed control 28 may only control the speed of the drive mechanism 30, with the drive mechanism 30 remaining active whenever the power cord 36 is receiving electrical power.

Once the desired frequency has been set and the shade 16 is rotating while the light source 14 is emitting light, a user can "view" the lamp 10 by placing his or her face about 5 to 20 cm from the shade 16 with his or her eyes closed.

In one embodiment, the frequency ranges are selected from below 4 Hz, which corresponds to a delta brainwave state, between about 4 to about 7 Hz, which corresponds to a theta brainwave state, between about 7 to about 13 Hz, which corresponds to an alpha brainwave state, and between about 13 to about 30 Hz, which corresponds to a beta brainwave state. Thus, a user can use the speed control to select flickering frequencies corresponding to one or more desired human brainwave states. In one particular embodiment, the lamp 10 is designed so that, depending on the setting of the speed control 28, the rotating shade will produce flickering between about 4 to 7 Hz (theta brainwave state) or between about 7 to 13 Hz (alpha brainwave state). Selection of the appropriate rotation speed of the shade 16 to produce a desired frequency, given a known size of the shade 16 and a known arrangement of circumferential width and circumferential spacing of the apertures 20 in the shade 16, is within the capability of one skilled in the art, now informed by the herein disclosure, as is configuration of the drive mechanism 30 to achieve the desired rotational speeds.

Figure 2B:
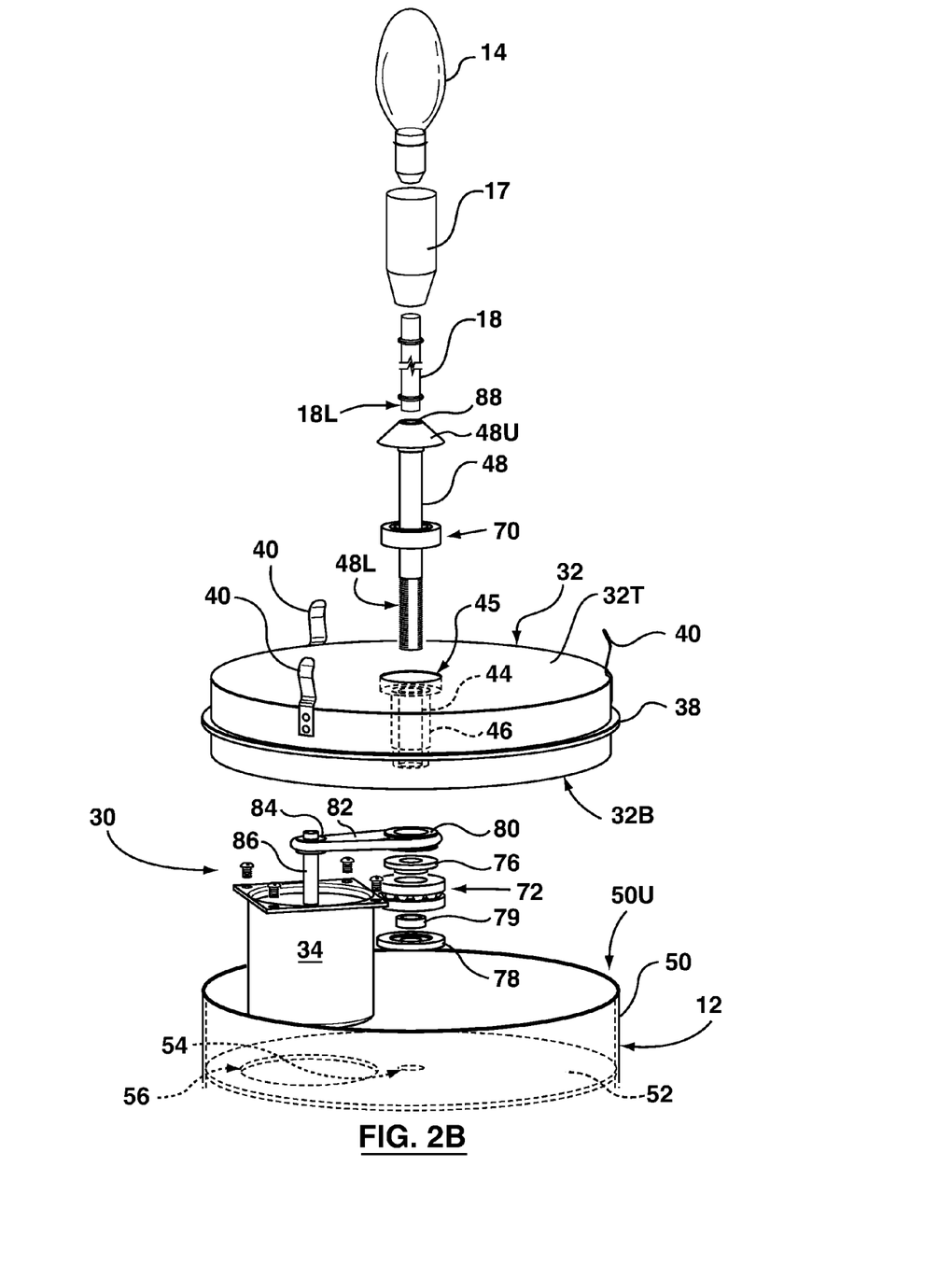
FIG. 2B is a more detailed exploded perspective view of a portion of the lamp of FIG. 1.

Now referring to FIG. 2B and FIG. 3, the exemplary drive mechanism 30 of the exemplary illustrated lamp 10 will be described in more detail. The drive mechanism 30 comprises a turntable 32 that carries the shade 16 and a motor 34 that drives the turntable 32. The turntable 32 is generally cylindrical and has a closed top end 32T and an open bottom end 32B. The turntable 32 has an outwardly extending annular flange 38 for supporting the lower edge 16LE of the shade 16, and a plurality of circumferentially spaced upwardly extending resilient tabs 40 are secured to the outer surface of the turntable 32. The resilient tabs 40 cooperate with an inwardly extending annular flange 42 (FIG. 3) on the inner surface of the shade 16, adjacent the lower bottom end 16L thereof, to bias the lower edge 16LE of the shade 16 into engagement with the upper surface of the outwardly extending annular flange 38 on the turntable 32. Thus, the shade 16 is removably retained on the turntable 32 so that the shade 16 rotates with the turntable 32. The turntable 32 includes a central aperture 44, a central receptacle 45 defined around the central aperture 44 and a downwardly depending sleeve 46 through which the central aperture 44 extends. The central receptacle 45 is defined by an annular shoulder 47 (FIG. 3) on the sleeve 46, with the annular shoulder 47 spaced downwardly from the closed top end 32T of the turntable 32. An upwardly extending guide shaft 48 that is supported by the base 12 is received within the sleeve 46, inside the central aperture 44 as described further below.

Figure 3:
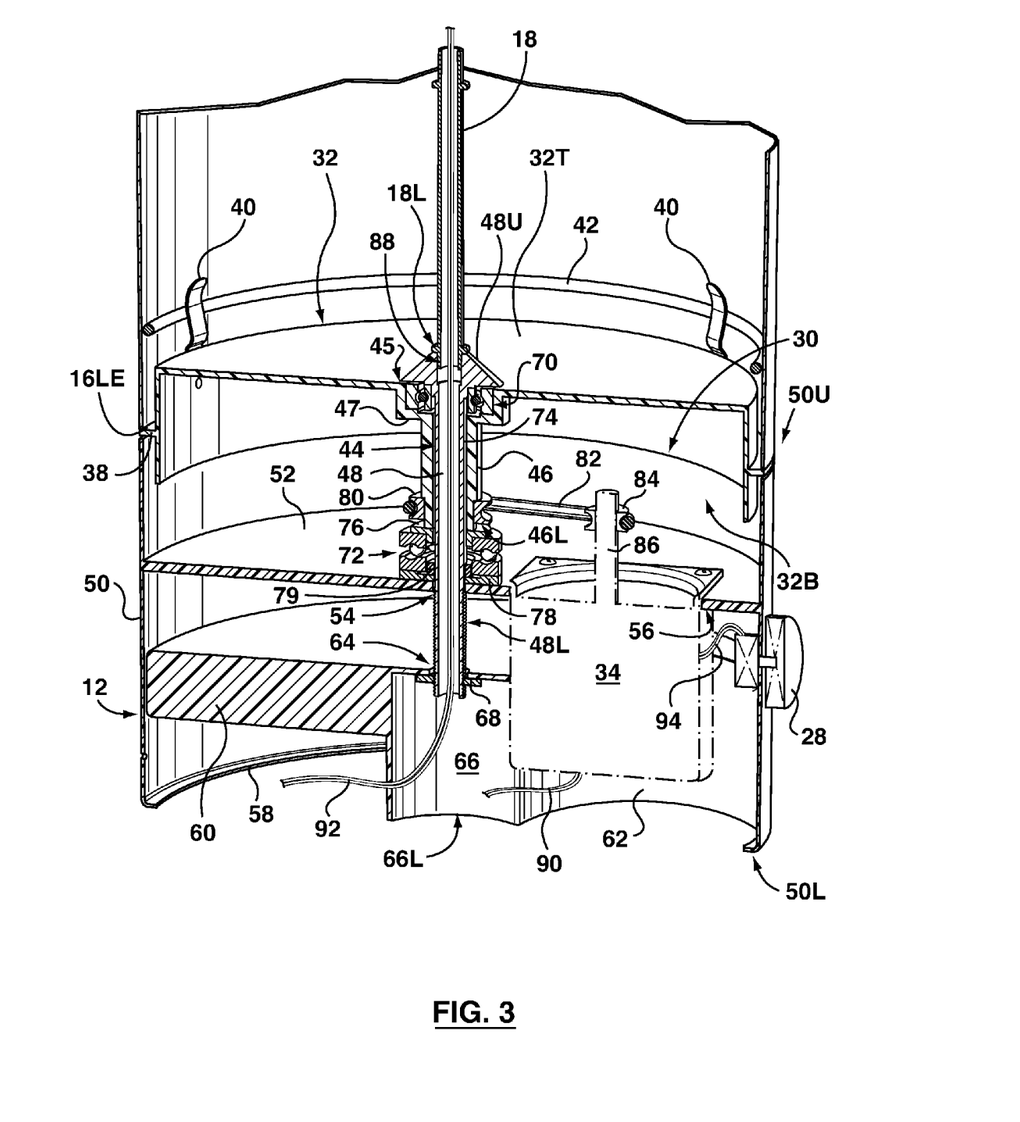
FIG. 3 is a cross-sectional view of a portion of the lamp of FIG. 1.

Referring specifically to FIG. 3, the base 12 comprises a hollow cylindrical outer housing 50 having an open upper end 50U, an open lower end 50L, and a circular cross-member 52 extending across the interior of the housing 50. The cross-member has a central shaft aperture 54 defined therethrough as well as a motor aperture 56 defined therethrough between the central shaft aperture 54 and the wall of the housing 50. The lower end 50L of the housing 50 includes an inwardly extending annular flange 58, and a receiver 60 is disposed inside the housing 50, supported on the inwardly extending annular flange 58. The receiver includes a cavity 62 to accommodate the motor 34 as well as a centrally disposed fastening aperture 64 that opens into a cylindrical well 66 that is open at its lower end 66L. The guide shaft 48 passes through the central shaft aperture 54 in the cross-member 52 and also through the fastening aperture 64 and is secured in position by a nut 68 threaded onto the threaded lower end 48L of the guide shaft 48. The open cylindrical well 66 facilitates fastening of the nut 68 on the threaded lower end 48L of the guide shaft 48.

As noted above, the guide shaft 48 is received within the sleeve 46, inside the central aperture 44 thereof; thus the sleeve 46 fits over the guide shaft 48 so that the turntable 32 can rotate about the guide shaft 48. The turntable 32 is supported on the guide shaft 48 by a radial ball bearing 70 and is supported on the cross-member 52 by a thrust or axial ball bearing 72. More specifically, the radial ball bearing 72 is received within the central receptacle 45, and the outer diameter of the guide shaft 48 is smaller than the inner diameter of the sleeve 46 so that the radial ball bearing 72 maintains an annular gap 74 between the inner surface of the sleeve 46 and the outer surface of the guide shaft 48. The radial ball bearing 72 is retained in position by the lower surface of the outwardly flared upper end 48U of the guide shaft 48, which engages the upper surface of the inner race of the radial ball bearing 72 but is spaced from the upper surface of the outer race of the radial ball bearing 72 to permit rotation of the turntable 32. The lower end 46L of the sleeve 46 engages a flanged fitting 76 received in the upper race of the axial ball bearing 72, and the lower race of the axial ball bearing 72 rests on an annular support member 78 that in turn rests on the cross-member 50. A spacer 79 extends between the guide shaft 48 and the lower race of the axial ball bearing 72.

The lower end 46L of the sleeve 46 is inwardly stepped and carries a driven pulley 80 that is drivingly coupled by a belt 82 to a drive pulley 84 carried by the drive shaft 86 of the motor 34. Thus, the sleeve 46 is a driven shaft that is driven by the motor 34 to rotate the turntable 32 and thereby rotate the shade 16 about the light source 14. The flanged lower end 18L of the spacer shaft 18, which carries the fitting 17 for the light source 14 (FIGS. 2A and 2B) is received in an aperture 88 in the flared upper end 48U of the guide shaft 48.

As noted above, a power cord 36 (not shown in FIG. 3) extends into the base 12. The power cord 36 is coupled to power connectors in the form of wires 90, 92 for supplying power to the motor 34 (and hence the drive mechanism 30) and to the light source 14, respectively, with the wires 92 for the light source passing through the hollow guide shaft 48 and hollow spacer shaft 18 to the fitting 17.

In the illustrated embodiment, the motor 34 is a variable speed motor and the speed control 28 is coupled to the drive mechanism 30 by being coupled to the motor 34, in particular by way of an electrical connection via wires 94, to control the speed of the motor 34. The motor 34 may rotate at a plurality of discrete speeds, in which case the speed control 28 can control the drive mechanism 30 and hence the rotational speed of the shade 16 by selecting one of the discrete speeds of the motor 34. Where the motor 34 can rotate within a continuous range of speeds, the speed control 28 can control the drive mechanism 30, and thus the rotational speed of the shade 16, by setting the motor 34 to run at a desired speed within the continuous range of rotational speeds.

In alternative embodiments, the drive mechanism may comprise a motor that rotates at a single speed, and control of the speed of rotation of the shade may be achieved by a variable speed mechanical transmission controlled by the speed control. The illustrated drive mechanism 30 shown and described herein is exemplary only, and other drive mechanisms may also be used. For example, the belt 82 and pulley 80, 84 connection between the motor 34 and the turntable 32 may be replaced with a geared connection or a chain and sprocket connection.

The light source 14 may be a single individual light element or may comprise a plurality of light elements, for example, one or more incandescent light sources or one or more light-emitting diodes (LEDs). The light source 14 may be of fixed or variable intensity, and may emit only a single color or selectably emit one of a plurality of colors. For example, where the light source 14 comprises a plurality of LEDs, the LEDs may be provided in a plurality of colors, and the color of light emitted by the light source 14 may be controlled by selective activation of the colored LEDs. In the illustrated embodiment, the light source 14 can emit light of variable intensity and light of multiple colors, and a light control 96 is integrated into the power cord 36 and electrically coupled to the light source 14 for activating and deactivating the light source 14 and for controlling the intensity and the color of the light source 14. Typically, the light control 96 will include suitable markings or other indicia to indicate the current intensity and/or color of light emitted by the light source 14.

Currently preferred embodiments have been described by way of example. It will be apparent to persons skilled in the art that a number of variations and modifications can be made without departing from the scope of the invention as defined in the claims.

The table below sets out a listing of the reference numerals used herein, as well as the part or feature identified by that reference numeral, for ease of reference. No limitation is implied by this table.

| Reference | Part/Feature Description |
| --- | --- |
| 10 | Lamp generally |
| 12 | Base of lamp generally |
| 14 | Light source |
| 16 | Cylindrical shade |
| 16U | Upper end of shade |
| 16C | Canopy across upper end of shade |
| 16L | Lower end of shade |
| 16LE | Lower edge of shade |
| 17 | Fitting for light source |
| 18 | Hollow spacer shaft |
| 18L | Flanged lower end of spacer shaft |
| 20 | Apertures in shade |
| 28 | Speed control |
| 30 | Drive mechanism generally |
| 32 | Turntable generally |
| 32T | Closed top end of turntable |
| 32B | Open bottom end of turntable |
| 34 | Motor |
| 36 | Power cord |
| 38 | Outwardly extending annular flange on turntable |
| 40 | Tabs on turntable |
| 42 | Inwardly extending annular flange on shade |
| 44 | Central aperture in turntable |
| 45 | Central receptacle in turntable |
| 46 | Downwardly depending sleeve on turntable |
| 46L | Lower end of sleeve |
| 47 | Annular shoulder on downwardly depending sleeve |
| 48 | Upwardly extending guide shaft supported by base |
| 48L | Threaded lower end of guide shaft |
| 48U | Flared upper end of guide shaft |
| 50 | Hollow cylindrical housing of base |
| 50U | Open upper end of cylindrical housing |
| 50L | Open lower end of cylindrical housing |
| 52 | Cross-member in cylindrical housing |
| 54 | Central shaft aperture in cross-member |
| 56 | Motor aperture in cross-member |
| 58 | Inwardly extending annular flange at lower end of cylindrical housing |
| 60 | Receiver inside housing |
| 62 | Motor cavity in receiver |
| 64 | Centrally disposed fastening aperture in receiver |
| 66 | Cylindrical well in receiver |
| 66L | Open lower end of cylindrical well in receiver |
| 68 | Nut |
| 70 | Radial ball bearing |
| 72 | Axial ball bearing |
| 74 | Annular gap between inner surface of sleeve and outer surface of guide shaft |
| 76 | Flanged fitting |
| 78 | Support member |
| 79 | Spacer |
| 80 | Driven pulley |
| 82 | Belt |
| 84 | Drive pulley |
| 86 | Drive shaft of motor |
| 88 | Aperture in upper end of guide shaft |
| 90 | Wires for supplying power to drive mechanism |
| 92 | Wires for supplying power to light source |
| 94 | Wires connecting speed control to motor |
| 96 | Light control |

What is claimed is:

1. A lamp for generating flickering at a selectable frequency corresponding to a desired human brainwave state, comprising:
   a base;
   a light source supported by the base;
   an opaque shade having a plurality of regularly circumferentially spaced apertures defined therein;
   the opaque shade circumferentially surrounding the light source and rotatably supported by the base for rotation about the light source;
   a drive mechanism supported by the base and drivingly coupled to the opaque shade for rotating the opaque shade about the light source;
   the drive mechanism and the light source coupled to at least one power connector for supplying power to the drive mechanism and the light source;
   wherein rotation of the opaque shade while the light source is emitting light produces binary flickering for an observer looking at the lamp from a fixed position;
   said binary flickering being produced by rotation of the apertures into and out of registration with a line of sight from the observer to the light source whereby:
      interposition of a non-apertured portion of the opaque shade in the line of sight obscures the light source from the observer and obstructs light from the light source from reaching the observer; and
      interposition of an aperture of the opaque shade in the line of sight permits light from the light source to reach the observer;
   the lamp further comprising at least one speed control coupled to the drive mechanism for controlling the drive mechanism to select a rotational speed of the opaque shade to selectively produce one of at least:
      binary flickering within a first predetermined frequency range corresponding to a first pre-selected human brainwave state; and
      binary flickering within a second predetermined frequency range corresponding to a second pre-selected human brainwave state;

the first and second pre-selected human brainwave states being different from one another.

2. The lamp of claim 1, wherein the first and second frequency ranges are selected from the group consisting of:
below 4 Hz wherein the corresponding pre-selected human brainwave state is a delta brainwave state;
between about 4 to about 7 Hz wherein the corresponding pre-selected human brainwave state is a theta brainwave state;
between about 7 to about 13 Hz wherein the corresponding pre-selected human brainwave state is an alpha brainwave state; and
between about 13 to about 30 Hz wherein the corresponding pre-selected human brainwave state is a beta brainwave state.

3. The lamp of claim 2, wherein:
the first predetermined frequency range is between about 4 to about 7 Hz and the corresponding first pre-selected human brainwave state is a theta brainwave state; and
the second predetermined frequency range is between about 7 to about 13 Hz and the corresponding second pre-selected human brainwave state is an alpha brainwave state.

4. The lamp of claim 1, wherein the drive mechanism comprises a variable speed motor and the at least one speed control is coupled to the drive mechanism by being coupled to the motor to control a speed of the motor.

5. The lamp of claim 4, wherein the at least one speed control controls the drive mechanism to select the rotational speed of the opaque shade from among a plurality of discrete rotational speeds.

6. The lamp of claim 4, wherein the at least one speed control controls the drive mechanism to select the rotational speed of the opaque shade from within at least one continuous range of rotational speeds.

7. The lamp of claim 1, wherein the at least one speed control controls the drive mechanism to select the rotational speed of the opaque shade to selectively produce one of:
binary flickering within the first predetermined frequency range corresponding to the first pre-selected human brainwave state;
binary flickering within the second predetermined frequency range corresponding to the second pre-selected human brainwave state; and
binary flickering within a third predetermined frequency range corresponding to a third pre-selected human brainwave state;
the third pre-selected human brainwave state being different from the first and second pre-selected human brainwave states.

8. The lamp of claim 7, wherein the first, second and third frequency ranges are selected from the group consisting of:
below 4 Hz wherein the corresponding pre-selected human brainwave state is a delta brainwave state;
between about 4 to about 7 Hz wherein the corresponding pre-selected human brainwave state is a theta brainwave state;
between about 7 to about 13 Hz wherein the corresponding pre-selected human brainwave state is an alpha brainwave state; and
between about 13 to about 30 Hz wherein the corresponding pre-selected human brainwave state is a beta brainwave state.

9. The lamp of claim 7, wherein the at least one speed control controls the drive mechanism to select the rotational speed of the opaque shade to selectively produce one of:
binary flickering within the first predetermined frequency range corresponding to the first pre-selected human brainwave state;
binary flickering within the second predetermined frequency range corresponding to the second pre-selected human brainwave state;
binary flickering within the third predetermined frequency range corresponding to the third pre-selected human brainwave state; and
binary flickering within a fourth predetermined frequency range corresponding to a fourth pre-selected human brainwave state;
the fourth pre-selected human brainwave state being different from the first, second and third pre-selected human brainwave states.

10. The lamp of claim 9, wherein the first, second, third and fourth frequency ranges are selected from the group consisting of:
below 4 Hz wherein the corresponding pre-selected human brainwave state is a delta brainwave state;
between about 4 to about 7 Hz wherein the corresponding pre-selected human brainwave state is a theta brainwave state;
between about 7 to about 13 Hz wherein the corresponding pre-selected human brainwave state is an alpha brainwave state; and
between about 13 to about 30 Hz wherein the corresponding pre-selected human brainwave state is a beta brainwave state.

11. The lamp of claim 1, wherein the light source comprises a single light element.

12. The lamp of claim 1, wherein the light source comprises a plurality of individual light elements.

13. The lamp of claim 1, wherein the light source is a variable intensity light source, further comprising a light control coupled to the light source for controlling an intensity of light emitted from the light source.

14. The lamp of claim 1, wherein the light source is a variable color light source, further comprising a light control coupled to the light source for controlling a color of light emitted from the light source.

15. The lamp of claim 1, wherein the light source comprises at least one incandescent light source.

16. The lamp of claim 1, wherein the light source comprises at least one light-emitting diode.

17. A lamp for generating flickering at a selectable frequency corresponding to a desired human brainwave state, comprising:
a base;
a light source supported by the base;
an opaque shade having a plurality of regularly circumferentially spaced apertures defined therein;
the opaque shade circumferentially surrounding the light source and rotatably supported by the base for rotation about the light source;
a drive mechanism supported by the base and drivingly coupled to the opaque shade for rotating the opaque shade about the light source;
the drive mechanism and the light source coupled to at least one power connector for supplying power to the drive mechanism and the light source;
wherein rotation of the opaque shade while the light source is emitting light produces binary flickering for an observer looking at the lamp from a fixed position;
said binary flickering being produced by rotation of the apertures into and out of registration with a line of sight from the observer to the light source whereby:

interposition of a non-apertured portion of the opaque shade in the line of sight obscures the light source from the observer and obstructs light from the light source from reaching the observer; and interposition of an aperture of the opaque shade in the line of sight permits light from the light source to reach the observer;

the lamp further comprising at least one speed control coupled to the drive mechanism for controlling the drive mechanism to select a rotational speed of the opaque shade to selectively produce binary flickering within one of a plurality of different predetermined frequency ranges, with each predetermined frequency range corresponding to a different pre-selected human brainwave state.

18. The lamp of claim 17, wherein the frequency ranges are selected from the group consisting of:

below 4 Hz wherein the corresponding pre-selected human brainwave state is a delta brainwave state;

between about 4 to about 7 Hz wherein the corresponding pre-selected human brainwave state is a theta brainwave state;

between about 7 to about 13 Hz wherein the corresponding pre-selected human brainwave state is an alpha brainwave state; and between about 13 to about 30 Hz wherein the corresponding pre-selected human brainwave state is a beta brainwave state.

19. The lamp of claim 17, wherein the at least one speed control controls the drive mechanism to select the rotational speed of the opaque shade from among a plurality of discrete rotational speeds.

20. The lamp of claim 17, wherein the at least one speed control controls the drive mechanism to select the rotational speed of the opaque shade from within at least one continuous range of rotational speeds.

\* \* \* \* \*